United States Patent [19]

Shimamura et al.

[11] 4,394,336

[45] Jul. 19, 1983

[54] PRODUCTION OF TABLETS OF SODIUM DICHLOROISOCYANURATE

[75] Inventors: Tadao Shimamura; Junji Nakano; Yasufumi Seo, all of Tokushima, Japan

[73] Assignee: Shikoku Kasei Kogyo Company Ltd., Marugame, Japan

[21] Appl. No.: 284,758

[22] Filed: Jul. 20, 1981

[30] Foreign Application Priority Data

Aug. 1, 1980 [JP] Japan .................................. 55-106604

[51] Int. Cl.$^3$ ............................................... A61J 3/10
[52] U.S. Cl. .................................................... 264/109
[58] Field of Search ........................................... 264/109

[56] References Cited

U.S. PATENT DOCUMENTS

| 3,956,444 | 5/1976 | Kibbel | 264/109 |
| 4,024,257 | 5/1977 | Kibbel | 264/109 |
| 4,261,942 | 4/1981 | Shimamura et al. | 264/109 |

Primary Examiner—Maurice J. Welsh
Attorney, Agent, or Firm—Jordan and Hamburg

[57] ABSTRACT

Production of tablets of sodium dichloroisocyanurate which dissolve gradually and smoothly in water without causing any undesirable collapse and swelling. The sodium dichloroisocyanurate with a regulated moisture content is tabletted and then the resulting tablets are thermally treated under specific conditions.

5 Claims, No Drawings

PRODUCTION OF TABLETS OF SODIUM DICHLOROISOCYANURATE

BACKGROUND OF THE INVENTION

1. Field of the Invention

The present invention relates to the production of tablets of sodium dichloroisocyanurate, and more particularly to the production of tablets which dissolve gradually and smoothly in water without causing any undesirable collapse and swelling.

Sodium dichloroisocyanurate is a very useful solid chlorine compound which is effective to release active chlorine for various purposes such as sterilizing water in swimming pools, human waste and sewerage.

2. Description of the Prior Art

Sodium dichloroisocyanurate has been used generally in the form of granules or tablets, but the latter form is more desirable in view of ease in its handling such as in storing, transportation and use.

Various processes have hitherto been proposed for the production of sodium dichloroisocyanurate in tablet form. For instance, Japanese Pat. No. 513 484 (Jap. Pat. Publn. No. 23198/1967) granted to the assignee of the present application, discloses a method wherein sodium dichloroisocyanurate powder is kneaded with sufficient water, the kneaded material with a predetermined water content is tabletted with a surface pressure of about 1000 Kg/cm$^2$ and then dried. U.S. Pat. Nos. 3,956,444 and 4,024,257 to William Kibbel, Jr. disclose a method wherein sodium dichloroisocyanurate dihydrate is compressed by a surface pressure of from about 2000 to about 10000 p.s.i. to obtain tablets. Further, U.S. Pat. No. 4,261,942 to Tadao SHIMAMURA et al and assigned to the assignee of the present application discloses a method wherein granular sodium dichloroisocyanurate with a moisture content of from 7 to 11 weight % is tabletted.

However, the tablets of sodium dichloroisocyanurate produced by any of such known methods collapse or swell remarkably within a very short time period, when they have been thrown into water, or contacted with sewerage water and the like to be sterilized.

When the conventional tablets are employed as the sterilizer for water, for instance in swimming pools, such phenomena may be advantageous in that the water can rapidly be sterilized within a relatively short time but disadvantageous in that the rapid dissolution of tablets tends to cause an excessive active chlorine concentration in the water, which means an increase of loss of the active chlorine due to rays of the sun and requires a great deal of labor in maintaining and controlling a desired active chlorine level in the water. Further, when the conventional tablets are filled in a cylindrical vessel to sterilize human waste water, the lower end of the vessel is immersed in the water, so that the water rises up in the vessel filled with the tablets due to a capillary action to cause a swelling of the tablets at a level above the water level external to the vessel; this may cause a blocking in the vessel to make impossible a uniform supply of active chlorine to the water being treated.

SUMMARY OF THE INVENTION

Accordingly, an object of the present invention is to provide a method of producing sodium dichloroisocyanurate tablets which can gradually and smoothly be dissolved in water without causing any undesirable collapse and swell.

According to the present invention, the above object and other objects which will be apparent from the following description are attained by tabletting sodium dichloroisocyanurate with a moisture content in the range of from about 7 to 20 weight %, and thermally treating the resulting tablets at a temperature ranging from about 50° to 100° C. under a condition such that the water content in each of said tablets is not lost by vaporization.

The exact mechanism by which the tablets produced according to the present invention do not cause any undesired collapse and swell has not yet sufficiently been elucidated, but it is considered by the inventors that, during the thermal treatment, the water present in each tablet dissolves sodium dichloroisocyanurate in the tablet. This is followed by recrystallization on cooling so as to result in fused adhesion of each crystal. It may be mentioned that the temperature of transition of sodium dichloroisocyanurate dihydrate into its monohydrate is about 65° C. The suggested mechanism is supported by the fact that the hardness of the tablets is markedly lowered during the thermal treatment but they become very hard upon cooling.

DETAILED DESCRIPTION OF THE PREFERRED EMBODIMENTS

Prior to carrying out the method according to the present invention, the moisture content of the sodium dichlorioisocyanurate should be regulated to be in the range of from 7 to 20 weight %. If the moisture content is less than about 7 weight %, it is difficult to eject tablets from a die of the tabletting machine and, if the moisture content is more than about 20 weight %, water exudes from the tablet surface.

It is preferable to use a tabletting pressure of about 350 Kg/cm$^2$ or more. If a lesser pressure is employed, the resulting tablets are not sufficiently strong and may be broken, for instance, during transportation.

The thermal treatment of the tablets is carried out at a temperature ranging from about 50° to 100° C., and more particularly from 65° to 80° C., to release at least a part of the crystal water. The thermal treatment should be carried out so as to prevent any loss by vaporization of the water contained in the tablets. When the tablets with a lower moisture content are treated, it is preferable to carry out the treatment in an atmosphere having a relative humidity in the range of 50% or more, in order to increase the moisture content of the tablets.

It is not desirable to carry out the thermal treatment at a temperature higher than 100° C., since the tablets are melted on their outer surfaces and become bonded together.

Sodium dichloroisocyanurate tablets produced according to the present invention show a bulk density lower than that of the corresponding tablets which have not been thermally treated. For instance, tablets which are formed by compacting granular sodium dichloroisocyanurate dihydrate (moisture content 14.1%) at the surface pressure of about 1000 Kg/cm$^2$ show generally a bulk density of 1.6 to 1.8 g/cm$^3$; but if such tablets are thermally treated for about 30 minutes in an air conditioned vessel kept at a temperature of about 80° C. and a relative humidity of 80%, the bulk density of the resulting tablets is changed to a value of 1.2 to 1.5 g/cm$^3$.

REFERENCE EXAMPLE 15 g of granular sodium dichloroisocyanurate with a moisture content of 7.9 weight % were charged into a die with a diameter of 30 mm and compacted at a surface pressure of about 1000 Kg/cm² to obtain a tablet. A similar operation was carried out by use of granular sodium dichloroisocyanurate with a moisture content of 13.12 weight % to obtain a corresponding tablet.

The tablets were put on a sieve with an opening of ½ inch and then immersed under water. The tablets collapsed and fell down from the sieve after the lapse of 270 and 350 seconds, respectively.

Another test was carried out in the following manner.

Two tablets were prepared by use of the raw materials with moisture contents of 7.9 and 13.12 weight % respectively, and in the manner as described above. The tablets constituting each pair were put in an Petri dish with a diameter of 100 mm in a overlapping manner and then 20 ml of water was poured into the dish so that the lower tablet is immersed with the water but the upper one is not immersed, so as to investigate the swelling phenomenon of the upper tablet in each pair.

In one hour, it was found that the upper tablets in each pair became swollen into sizes of 47 and 37 mm in diameter, respectively.

EXAMPLE 1

15 g of granular sodium dichloroisocyanurate with a moisture content of 13.12 weight % were charged into a die with a diameter of 30 mm, compacted at a surface pressure of about 1000 Kg/cm² to form a tablet. The resulting tablet was thermally treated for 30 minutes in an air conditioned vessel at 80° C. and with a relative humidity of 80%. The resulting tablet showed a moisture content of 14.1 weight %.

The test for collapsibility in water was carried out in the manner similar to that disclosed in the Reference Example and showed that that the tablet does not collapse and is uniformly and gradually dissolved in water; it requires about 80 minutes until it is dissolved completely.

Further, the swelling test was carried out in a manner similar to that disclosed in the Reference Example over a period of 48 hours. As a result, some absorption of water was found but no noticeable increase in diameter and height of the tablet could be observed.

EXAMPLE 2

15 g of granular sodium dichloroisocyanurate with a moisture content of 14.04 weight % were charged into a die and compacted at a surface pressure of about 1000 Kg/cm² to obtain a tablet. The tablet was inserted in a polyethylene bag and sealed therein. The sealed tablet was thermally treated for 40 minutes at about 80° C. The resulting tablet showed a moisture content of 14.01 weight %.

The test for collapsibility in water was carried out in a manner similar to that disclosed in the Reference Example. The tablet dissolved gradually and smoothly in water without any collapse; it required about 75 minutes for its complete dissolution.

The swelling test carried out in a manner similar to that disclosed in the Reference Example, showed that after the testing period of 48 hours, no noticeable swelling could be found on the tablet.

EXAMPLE 3

15 g of granular sodium dichlorioisocyanurate with a moisture content of 7.61 weight % were charged into a die, compacted at a surface pressure of about 1000 Kg/cm². The resulting tablet was thermally treated for 35 minutes under air conditioning at 80° C. and a relative humidity of 90%. The resulting tablet showed a moisture content of 15.2 weight %.

The test for collapsibility in water was carried out in a manner similar to that disclosed in the Reference Example. The tablet dissolved gradually and smoothly in water without any collapse; it required about 80 minutes for its complete dissolution.

Further, the swelling test was also carried out in a manner similar to that disclosed in the Reference Example. There was no noticeable swell at the end of the testing period of 48 hours.

We claim:

1. A method of producing sodium dichloroisocyanurate tablets capable of gradually and smoothly dissolving in water, comprising tabletting particulate sodium dichloroisocyanurate with a moisture content of from about 7 to about 20 weight %, and thermally treating the resulting tablets at a temperature of from about 50° to about 100° C. under a condition such that the water content in said tablets is not lost by vaporization.

2. A method as claimed in claim 1, wherein the thermal treatment is carried out with hot air having a relative humidity of at least about 50%.

3. A method as claimed in claim 1, wherein sodium dichloroisocyanurate with a moisture content of from about 14 to about 20 weight % is tabletted and then the resulting tablets are thermally treated at a temperature of from about 50° to about 100° C. with hot air.

4. A method as claimed in claim 1, wherein sodium dichloroisocyanurate with a moisture content of from about 7 to about 14 weight % is tabletted and then the resulting tablets are thermally treated with hot air having a relative humidity of at least about 50%.

5. A method as claimed in claim 1, wherein the formed tablets are heated at a temperature ranging from about 65° to about 80° C.

* * * * *